US010018620B2

(12) United States Patent
Charest et al.

(10) Patent No.: US 10,018,620 B2
(45) Date of Patent: Jul. 10, 2018

(54) MICROFLUIDIC TISSUE MODEL

(71) Applicant: The Charles Stark Draper Laboratory, Inc., Cambridge, MA (US)

(72) Inventors: Joseph L. Charest, Cambridge, MA (US); Else Frohlich, Brookline, MA (US); Christopher DiBiasio, Stoughton, MA (US); Kenneth Vandevoordt, Medford, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 106 days.

(21) Appl. No.: 14/688,678

(22) Filed: Apr. 16, 2015

(65) Prior Publication Data

US 2015/0301027 A1 Oct. 22, 2015

Related U.S. Application Data

(60) Provisional application No. 61/980,398, filed on Apr. 16, 2014.

(51) Int. Cl.
*B01L 3/00* (2006.01)
*B01L 1/00* (2006.01)
(Continued)

(52) U.S. Cl.
CPC .......... *G01N 33/5023* (2013.01); *C12M 23/16* (2013.01); *C12M 41/00* (2013.01); *C12M 41/36* (2013.01)

(58) Field of Classification Search
CPC ...... C12M 25/02; C12M 25/10; C12M 25/14; B01L 3/5027; B01L 2200/06; B01L 2200/0642
See application file for complete search history.

(56) References Cited

U.S. PATENT DOCUMENTS

2003/0077204 A1* 4/2003 Seki ................ B01F 5/0471
422/70
2007/0212773 A1 9/2007 Fujii et al.
(Continued)

FOREIGN PATENT DOCUMENTS

JP 2009-133668 A 6/2009
JP 2011-528232 A 11/2011
(Continued)

OTHER PUBLICATIONS

International Search Report and Written Opinion dated Jul. 20, 2015 in PCT Application No. PCT/US2015/026190.
(Continued)

*Primary Examiner* — Nathan A Bowers
(74) *Attorney, Agent, or Firm* — McDermott Will & Emery LLP

(57) ABSTRACT

The present disclosure describes systems and methods for mimicking body tissue and the function thereof. The mimicked body tissue can include kidney tissue, the blood brain barrier, and other tissues. In some implementations, the systems described herein are used to test the impact of controlled factors on the tissue. The controlled factors can include flow rates, shear rates, and test chemicals (e.g., therapeutics and toxins). In some implementations, the system and methods are used to test pharmaceutical and biological therapies, characterize healthy or diseased tissue, and observe phenomena of the tissue in vitro.

11 Claims, 6 Drawing Sheets

(51) Int. Cl.
*G01N 33/00* (2006.01)
*G01N 33/50* (2006.01)
*C12M 3/06* (2006.01)
*C12M 1/34* (2006.01)

(56) References Cited

U.S. PATENT DOCUMENTS

| | | |
|---|---|---|
| 2010/0203578 A1 | 8/2010 | Geiger et al. |
| 2011/0082563 A1 | 4/2011 | Charest et al. |
| 2011/0250585 A1* | 10/2011 | Ingber .................. C12N 5/0696 435/5 |
| 2013/0053425 A1 | 2/2013 | To et al. |
| 2013/0203086 A1 | 8/2013 | Achyuta et al. |
| 2013/0230911 A1 | 9/2013 | Charest et al. |
| 2014/0065660 A1* | 3/2014 | Kim ....................... C12M 35/08 435/29 |
| 2014/0120633 A1 | 5/2014 | Gandini et al. |

FOREIGN PATENT DOCUMENTS

| | | |
|---|---|---|
| JP | 2013-506434 A | 2/2013 |
| JP | 2014-506801 A | 3/2014 |
| WO | WO-2010/009307 A2 | 1/2010 |
| WO | WO-2012/118799 A2 | 9/2012 |
| WO | WO-2015/032889 | 3/2015 |

OTHER PUBLICATIONS

Office Action dated Nov. 2, 2017 in European Patent Application No. 15720517.0.
Office Action dated Jan. 25, 2018 in Japanese Patent Application No. 2016-562904, and English translation thereof.

* cited by examiner

MICROFLUIDIC TISSUE MODEL

CROSS-REFERENCE TO RELATED APPLICATIONS

This application claims priority to U.S. Provisional Patent Application No. 61/980,398 filed on Apr. 16, 2014 and titled "Microfluidic Tissue Model," which is herein incorporated by reference in its entirety.

BACKGROUND

The modeling of tissue barriers, such as those formed by epithelial and endothelial cells in the vessels of the kidney and the blood brain barrier, is important for the development of pharmaceutical and other therapies. To measure cellular properties of the modeled tissues, culture systems use external monitoring devices, which are disadvantageous because the electrodes and other sensors are manually placed in position and the culture devices must be handled and removed from incubation to be measured. The manual placement of the sensors can affect readings if inconsistently placed. Also, placement of the sensors disturbs the tissue, which results in artifacts in the recordings.

SUMMARY OF THE DISCLOSURE

According to one aspect of the disclosure, a culture device includes a first layer defining a first microfluidic channel. The device also includes a second layer defining a second microfluidic channel. A membrane separates the first microfluidic channel of the first layer from the second microfluidic channel of the second layer. The device also includes a first graduated microfluidic channel in fluidic communication with the first microfluidic channel. The device further includes at least one electrode disposed in at least one of the first microfluidic channel and the second microfluidic channel.

In some implementations, the first layer and the second layer are polymer layers that include a thermoplastic, such as a cyclic olefin copolymer. In some implementations, the device also includes a second graduated microfluidic channel in fluidic communication with the second microfluidic channel. In some implementations, at least two electrodes are disposed in each of the first microfluidic channel and the second microfluidic channel.

In some implementations, a height of the first graduated microfluidic channel is between about $1/8$ and about $2/3$ of a height of the first microfluidic channel and a height of the second graduated microfluidic channel is between about $1/8$ and about $2/3$ of a height of the second microfluidic channel. A transition between an inlet of the first microfluidic channel and the first microfluidic channel that is gradual and has an angle between about 10 degrees and about 30 degrees with respect to the membrane. In some implementations, a thickness of the at least one electrodes is between about 0.5 µm and about 5 µm.

In some implementations, the membrane includes a micropatterned surface. The at least one electrode is configured to measure a trans-epithelial electrical resistance across the membrane. In some implementations, the device also includes an imager and at least one valve to control a fluid flow into the first microfluidic channel and the second microfluidic channel.

According to another aspect of the disclosure, a method for culturing tissue includes providing a culture device. The culture device includes a first layer that defines a first microfluidic channel and a first graduated microfluidic channel and a second layer that defines a second microfluidic channel and a second graduated microfluidic channel. The device also includes a membrane that separates the first microfluidic channel from the second microfluidic channel. The device also includes a plurality of electrodes that are disposed in at least one of the first microfluidic channel and the second microfluidic channel. The method also includes seeding a plurality of cells on the membrane. Once the cells are seeded onto the membrane a first cellular property is measured with the plurality of electrodes, and a fluid volume in at least one of the first graduated microfluidic channel and the second microfluidic channel is also measured.

In some implementations, the method also includes measuring a velocity of a fluid flow in at least one of the first graduated microfluidic channel and the second graduated microfluidic channel. Measuring the velocity of the fluid flow includes measuring a movement of an air-fluid interface in at least one of the first graduated microfluidic channel and the second graduated microfluidic channel. In some implementations, the cellular property is trans-epithelial electrical resistance. In some implementations, when measuring the velocity of the fluid flow one or more valves are closed to close an inlet and an outlet of each of the first microfluidic channel and the microfluidic channel.

In some implementations, the method also includes exposing the plurality of cells to at least one of a predetermined shear stress and a pharmaceutical agent, and then measuring a second cellular property of the plurality of cells.

In some implementations, the change of the fluid volume in the at least one of the first graduated microfluidic channel and the second microfluidic channel correlates to a volume of a fluid flow through the membrane.

The method also includes, in some implementations, injecting a tracer molecule into the first microfluidic channel, and then measuring a concentration of the tracer molecule in the second microfluidic channel.

In some implementations, the first layer and the second layer include thermoplastic, such as a cyclic olefin copolymer. In certain implementations, at least two electrodes are disposed in each of the first microfluidic channel and the second microfluidic channel. A height of the first graduated microfluidic channel is between about $1/8$ and about $2/3$ of a height of the first microfluidic channel and a height of the second graduated microfluidic channel is between about $1/8$ and about $2/3$ of a height of the second microfluidic channel. In some implementations, the membrane includes a micropatterned surface.

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description of the invention.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure describes systems and methods for mimicking body tissue and the function thereof. The mimicked body tissue can include kidney tissue, the blood brain barrier, lung tissue, gastro-intestinal tissue, skin tissue, and other tissues. In some implementations, the systems described herein are used to test the impact of controlled factors on the tissue. The controlled factors can include flow rates, shear rates, topographical patterns, and test chemicals (e.g., therapeutics and toxins). In some implementations, the system and methods are used to test pharmaceutical and biological therapies, characterize healthy or diseased tissue, and observe phenomena of the tissue in vitro.

Figure 1:
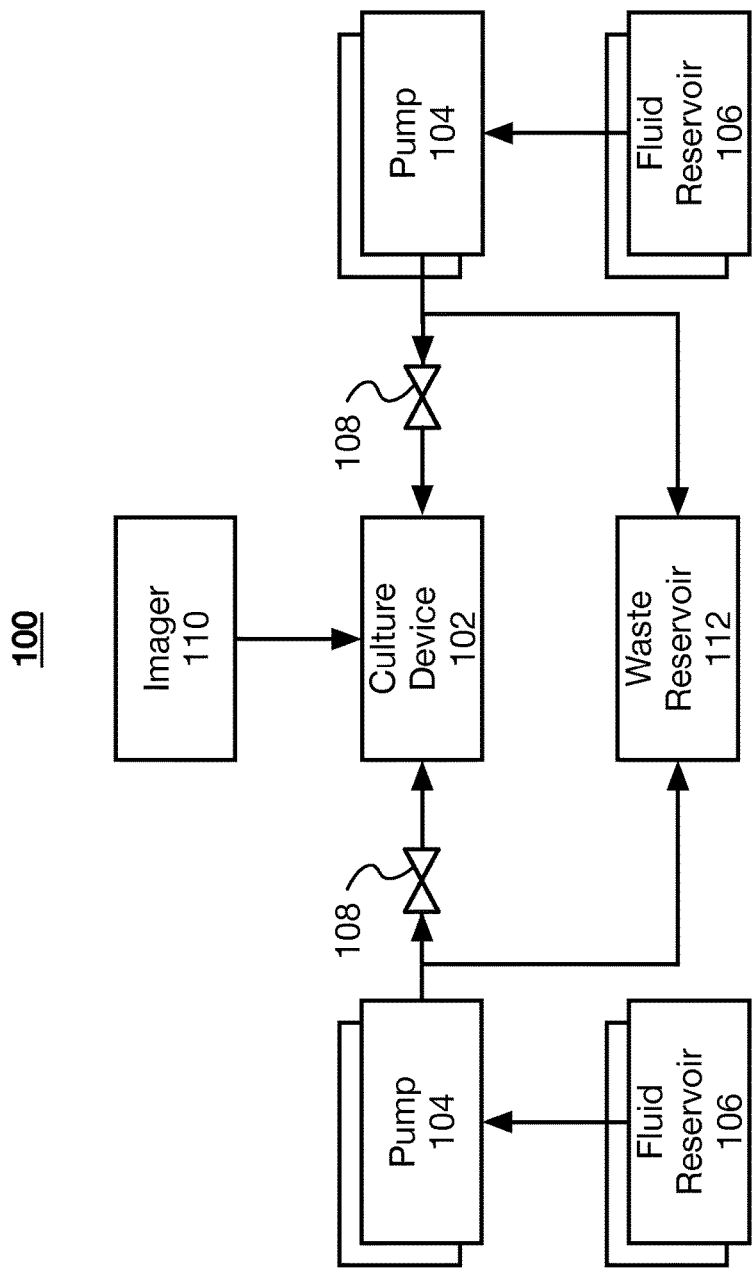
FIG. 1 illustrates an example system for microfluidic tissues modeling.

FIG. 1 illustrates an example system 100 for microfluidic tissues modeling. The system includes a culture device 102. The system 100 also includes a plurality of pumps 104 that flow fluid through the culture device 102 from respective fluid reservoirs 106. The fluidic lines between the pumps 104 and the culture device 102 include fluidic valve 108 to control the flow of fluid into the culture device 102. The system 100 also includes a waste reservoir 112. The system 100 includes an imager 110 to view cells within the culture device 102 and the operation of the culture device 102.

The culture device 102 of the system 100 is described in greater detail in relation to FIGS. 2-5. As an overview, the culture device 102 includes a first layer that defines one or more microfluidic channels and a second layer that also defines one or more microfluidic channels. A membrane is sandwiched between the first and second layers of the culture device 102. Cells are cultured on the membrane and the walls of the microfluidic channels while cell culture media, therapeutic agents, and other chemicals flow through the microfluidic channels of the culture device 102 and over the cells. The culture device 102 also includes one or more graduated microfluidic channels that are in fluidic communication with the at least one of the first and the second microfluidic channels. The culture device 102 also includes sensors, such as electrodes, to measure cellular properties of the cells.

As discussed above, the system 100 includes a number of components to support the culture device 102. The system 100 includes a plurality of pumps 104 that are configured to drive fluid from a respective fluid reservoir 106 through the culture device 102. In some implementations, the fluid reservoir 106 is any fluid containing vessel. In some implementations, the fluid reservoir 106 is a transwell or well plate housing a mixture of fluid and cells. In some implementations, the pumps 104 are peristaltic pumps or syringe pumps. In some implementations, each of the plurality of pumps 104 is a different type of pump. For example, the microfluidic channels can be coupled to a peristaltic pump and the graduated microfluidic channels can be coupled to a syringe pump. The pumps 104 control the fluid flowing through the culture device 102. For example, the pump 104 can control the fluid's flow rate, flow profile (e.g., whether the flow is pulsatile or smooth), and shear rate. In some implementations, the flow is continuous and in other implementations the flow is pulsatile. The fluids of the fluid reservoirs 106 that pass through the culture device 102 can include, but are not limited to, cell culture medium, cell nutrients, reagents, test agents, buffer fluids, tracer particles, gases, reactant fluids, fixing agents, stains, simulated and real biological fluids such as blood filtrate, whole blood, blood serum, blood plasma, urine, dilute urine.

In some implementations, the pumps 104 are configured to flow fluid in a first direction in the microfluidic channels above the membrane and in a second direction in the microfluidic channels below the membrane. In other implementations, the flows in the microfluidic channels above and below the membrane are in the same direction.

The system 100 also includes a waste reservoir 112. The waste reservoir 112 collects fluid exiting the culture device 102. In some implementations, the system 100 does not include the waste reservoir 112, and the system 100 is a closed-loop system. In these implementations, fluid exiting an outlet of the culture device 102 can be routed back into an inlet of the culture device 102.

The valves 108 of the system 100 control flow into and out of each of microfluidic channels of the culture device 102. In some implementations, the valves 108 are configured to close the input and output flow pathways to the microfluidic channels. Closing the flow pathways into and out of the microfluidic channels causes any change in volume in the microfluidic channels (for example from transport across the membrane separating two microfluidic channels) to be directed into the graduated microfluidic channels of the culture device 102. As described below, the directed flow into the graduated microfluidic channels enables the measurement of flow and pressure in the microfluidic channels of the culture device 102.

The imager 110 of the system 100 is used to observe cells within the culture device 102 and to visualize the graduated microfluidic channels. In some implementations, the cells are imaged while fluid is flowing through the culture device 102. In other implementations, at the end of an experiment, a fixing fluid is passed through the culture device 102 and the cells are imaged upon completion of experimentation. As described below, the graduated microfluidic channels are configured to measure the flow rate and pressure within the microfluidic channels of the culture device 102. In some implementations, the flow and pressure rates are measured by monitoring the movement of a gas bubble or tracer particle through the graduated microfluidic channels. The imager 110 is configured to enable a user to visualize the gas bubble or tracer practice present in the graduated microfluidic channel.

Figure 2:
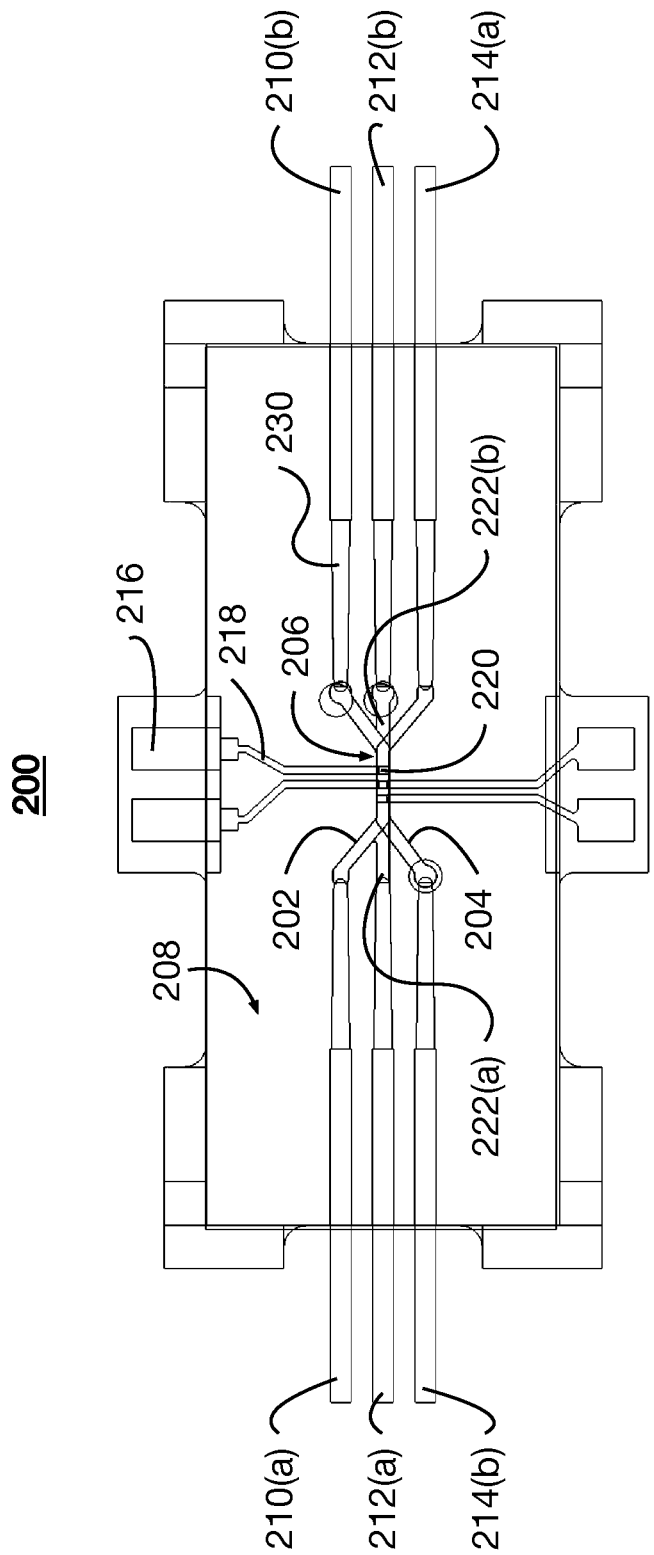
FIG. 2 illustrates a top view of an example culture device for use with the system illustrated in FIG. 1.

FIG. 2 illustrates a top view of an example culture device 200 for use with the system 100. As an overview of the assembled culture device 200, the culture device 200 includes a first microfluidic channel 202 in a first layer and a second microfluidic channel 204 in a second layer. The first microfluidic channel 202 and the second microfluidic channel 204 overlap one another over region 206. A membrane 208 is sandwiched between the first layer and the second layer and separates the first microfluidic channel 202 from the second microfluidic channel 204. A first graduated microfluidic channel 222(a) is coupled to the first microfluidic channel 202 and a second graduated microfluidic channel 222(b) is coupled to the second microfluidic channel 204. The culture device 200 also includes a plurality of electrodes 220 in each of the first microfluidic channel 202 and the second microfluidic channel 204. The electrodes 220 of the culture device 200 are electrically coupled to a plurality of contact pads 216 via traces 218. The electrodes 220, the first layer, and the second layer are also described further in relation to FIG. 3.

Still referring to FIG. 2, the first microfluidic channel 202 of the culture device 200 includes an inlet 210(a) and an outlet 214(a). A graduated microfluidic channel 222(a) is fluidically coupled to the first microfluidic channel 202. The graduated microfluidic channel 222(a) is coupled to a microfluidic port 212(a). The graduated microfluidic channels 222 are described in greater detail in relation to FIG. 4. The second microfluidic channel 204 of the culture device 200 is fluidically coupled to an inlet 210(b), an outlet 214(b), and a graduated microfluidic channel 222(b). A microfluidic port 212(b) is fluidically coupled to the graduated microfluidic channel 222(b). As illustrated in FIG. 2, the inlets 210(a) and 210(b) of the first microfluidic channel 202 and the second microfluidic channel 204, respectively, are located on opposite ends of the culture device 200 such that the flow of fluid through the first microfluidic channel 202 is opposite to the flow of fluid through the second microfluidic channel 204. In addition to flowing fluid through the inlets 210 and outlets 214, in some implementations, cells or tissue are seeded into the first microfluidic channel 202 and/or second microfluidic channel 204 by flowing the cells though the inlets 210. The culture device 200 also includes a transition region 230 that couples each of the first microfluidic channel 202, the second microfluidic channel 204, and the graduated microfluidic channels 222 to their respective inlets 210, outlets 214, and microfluidic ports 212. As described in relation to FIG. 4, the transition regions 230 are configured to prevent clumping of the cells seeded into the culture device 200. In some implementations, the microfluidic ports 212 are used to inject test agents such as, but not limited to, pharmaceuticals, toxins, tracer chemicals, or any combination thereof into the first microfluidic channel 202 and/or second microfluidic channel 204.

In some implementations, the first layer 224, second layer 226, and the membrane 208 are coupled together with claims so the layers of the culture device 200 are separable after an experiment. In other implementations, each of the layers of the culture device 200 are coupled together with a permeant adhesive (e.g., RTV), hot-melt adhesives (e.g., 3M Scotch-Weld 3738 and 3762), plasmas bonding, ultrasonic welding, friction welding, or laser welding.

Figure 3:
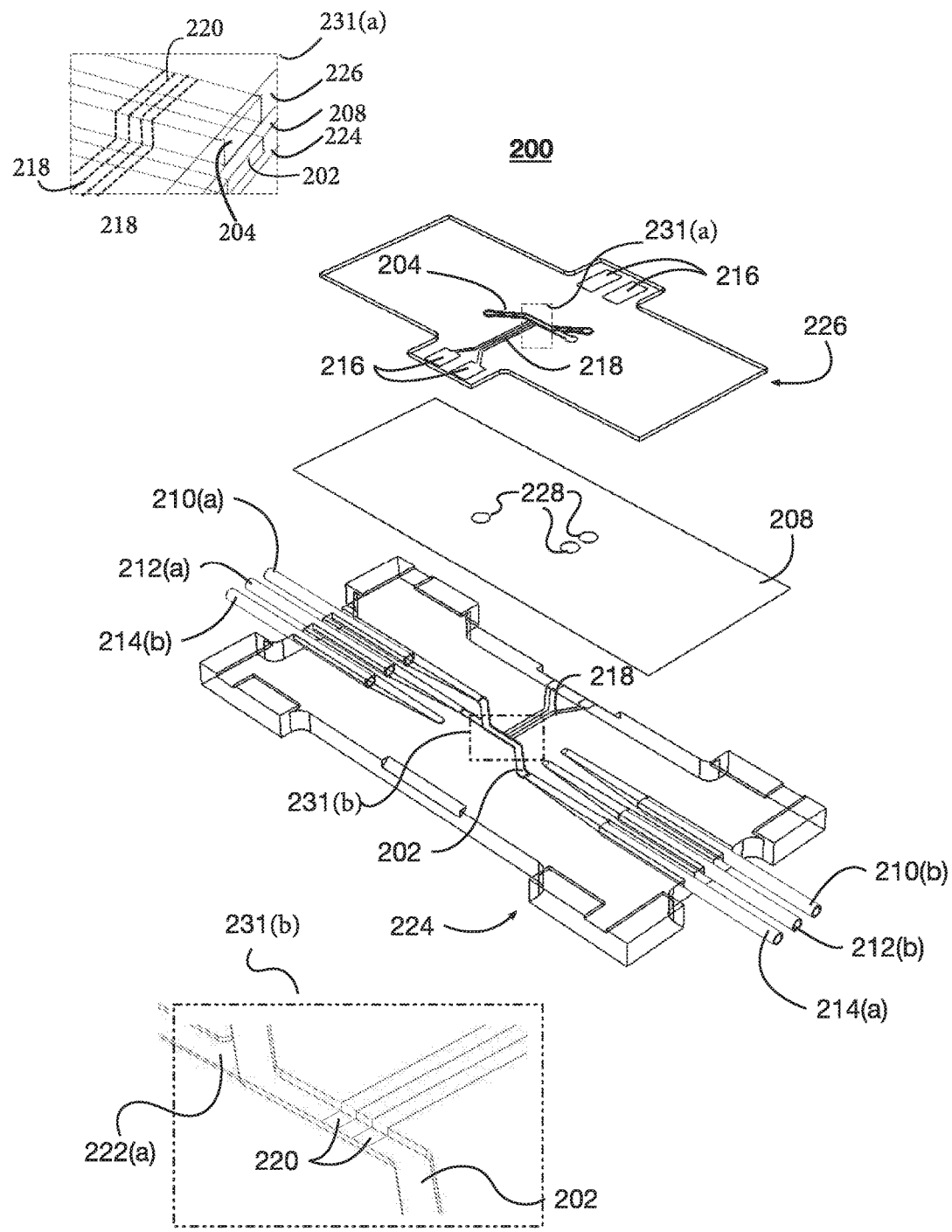
FIG. 3 illustrates an exploded view of the example culture device illustrated in FIG. 2.

FIG. 3 illustrates an exploded view of the example culture device 200. As described above, the culture device 200 includes a first layer 224 that defines the first microfluidic channel 202 and a second layer 226 that defines the second microfluidic channel 204. The membrane 208 is sandwiched between the first layer 224 and the second layer 226. FIG. 3 also illustrates an enlarged view of box 231(b), which illustrates the electrodes 220 running along a wall of the first microfluidic channel 202 and then along the floor of the first microfluidic channel 202. FIG. 3 also illustrates an enlarged view of box 231(a), which illustrates the electrodes 220 running along a wall of the second microfluidic channel 204 and then along the floor of the second microfluidic channel 204.

The first layer 224 and the second layer 226 define the microfluidic channels of the culture device 200. In some implementations, the first layer 224 and the second layer 226 are formed through molding, cutting, machining, or printing with an addictive process. In some implementations, the material of the first layer 224 and the second layer 226 is a thermoplastic, such as, but not limited to, cyclic olefin copolymers such as Zeonor, polystyrene, glass, polymethylmethacrylate, polycarbonate, and polyethylene polyethersulfone, polysulfone, Ultem, polyethylene teraphthalate, polyimide, and biodegradable plastics, such as polycaprolactone, polylactic acid, and polyglycerol sebacate. In some implementations, a thermoplastic is selected for the first layer 224 and the second layer 226 because the thermoplastic does not substantially absorb or release water soluble factors; provides optical clarity to enable visualization of the graduated microfluidic channels and cells or other tissue within the culture device 200; allows the transmission of ultraviolet light therethrough; and is biocompatible and does not interfere with cellular survival or other cellular processes.

As described above, the culture device 200 also includes a membrane 208 positioned between the first layer 224 and the second layer 226. In some implementations, as illustrated in FIG. 3, the membrane 208 has substantially the same sized footprint as the first layer 224 and the second layer 226. In other implementations, the membrane 208 is smaller and is only placed placed where the first microfluidic channel 202 and the second microfluidic channel 204 overlap. The membrane 208 includes a plurality of cutouts 228. The fluid flow into and out of the culture device 200 occurs through the first layer 224. The cutouts 228 enable fluid to flow to the second layer 226 and the microfluidic channels defined therein without filtering through the membrane 208.

In some implementations, the membrane 208 of the culture device 200 is a membrane made of a thermoplastic, such as polystyrene, polycarbonate, polyimide, polysulfone, polyethersulfone; biodegradable polyesters, such as polycaprolactone (PCL); soft elastomers, such as polyglycerol sebacate (PGS); or other polymers such as polydimethylsiloxane (PDMS) and poly(N-isopropylacrylamide). In other implementations, the membrane 208 is made from silicon, glass, or silicon nitride. In some implementations, the membrane 208 is micro patterned to include, for example, a plurality of ridges, posts, or pits, along one or more surfaces of the membrane 208. In some implementations, in addition to, or in place of, the micropattern the membrane 208 includes a plurality of pores defined through the membrane 208. The membrane 208 (and miropattern and pores thereof) is manufactured, in some implementations, through processing methods such as track-etching, electro-spinning, microfabrication, micromolding, gel deposition, phase separation, particle leaching, and solvent leaching. In yet other implementations, the membrane 208 is a multilayered membrane that includes several layers of material.

Still referring to FIG. 3, the culture device 200 also includes a plurality of electrodes 220. Each of the first microfluidic channel 202 and the second microfluidic channel 204 each include a pair of electrodes 220. In some implementations, only one of the first microfluidic channel 202 and the second microfluidic channel 204 include electrodes 220. The electrodes 220 are configured to stimulate and record electrical signals to, for example, generate a trans-endothelial resistance (TEER) profile. TEER is used, in some implementations, to measure the integrity and health of the tissues cultured in the culture device 200. For example, the electrodes 220 can be used to measure the impedance of a cell layer (or cell mat) grown on the membrane 208 to evaluate the barrier function of the cell layer. The electrodes 220, traces 218, and pads 216 include silver, stainless steel, platinum, chromium-gold alloys, or a combination thereof.

In some implementations, the electrodes 220 are formed by depositing a metal onto the first layer 224 and/or the second layer 226. The metal that forms the electrodes 220 is deposited onto a first wall, a floor (or roof), a second wall, a membrane between the first and second layers, or any combination thereof. In some implementations, the electrodes 220 are circular, rectangular, square, oval, or any other shape. In some implementations, a metal layer is deposited on substantially the entire floor (or roof) of the first microfluidic channel 202 and second microfluidic channel 204 to form the electrodes 220 that run substantially the length of the first microfluidic channel 202 and second microfluidic channel 204. In some implementations, each microfluidic channel of the culture device 200 includes between about 2 and about 20 electrodes, between about 2 and about 15, between about 2 and about 10, or between about 2 and about 6 electrodes. The electrodes 220 have a width (or diameter) between about 150 µm and about 500 µm, between about 150 µm and about 400 µm, or between about 200 µm and about 300 µm. The thickness of the electrodes 220 and traces 218 is between about 0.5 µm and about 30 µm, between about 0.5 µm and about 20 µm, between about 0.5 µm and about 15 µm wide, between about 0.5 µm and about 10 µm, or between about 0.5 µm and about 5 µm. The thickness of the electrodes 220 is selected such that as fluid flows over the culture device 200 substantially no turbulence is generated.

The electrodes 220 of the culture device 200 are connected to the pads 216 via the traces 218. The pads 216 are electrically coupled to external electrical measurement and stimulation equipment such as impedance meters, voltmeters, oscilloscopes, pulse generators, or a combination thereof.

Figure 4:
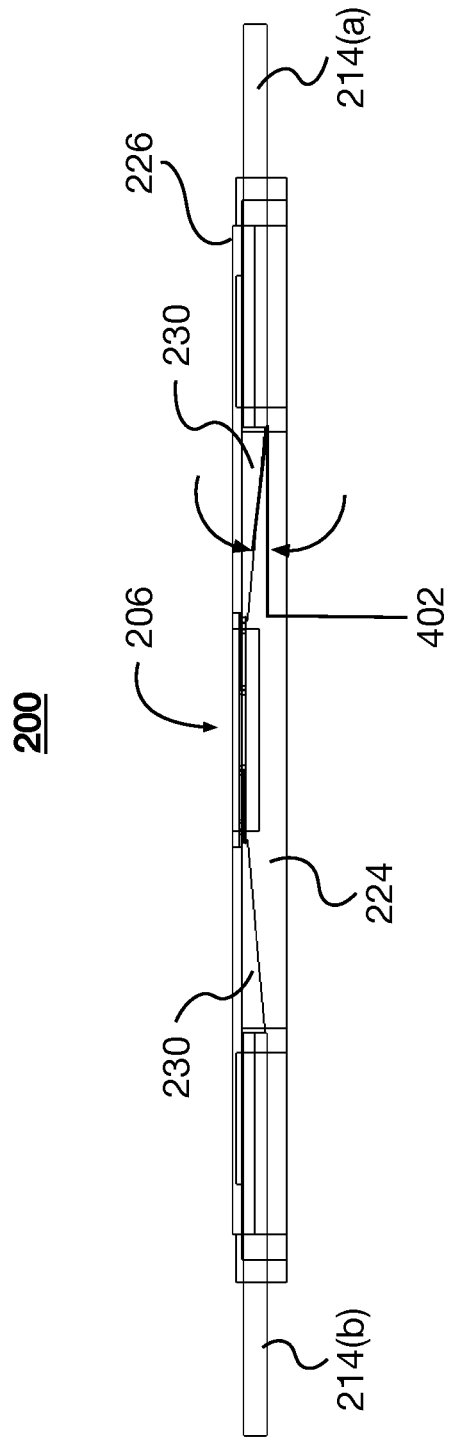
FIG. 4 illustrates a side view of the example culture device illustrated in FIG. 2.

FIG. 4 illustrates a side view of the culture device 200. As described above in relation to FIG. 2, a transition region 230 exists between the inlets 210, the microfluidic ports 212, the outlets 214 and their respective microfluidic channel or graduated microfluidic channel. The transition regions 230 are configured to enable seeding of cells within the microfluidic channels of the culture device 200 without damaging the cells or causing the cells to clump. For example, if the transition region 230 included a right angle, cells could bunch in the transition region 230. The cells bunched in the transition region 230 may then consume much of the growth media that is flowed through the microfluidic channels and cells in the center of the microfluidic channels may not receive enough nutrients to remain healthy. In some implementations, the angle 402 that the transition region 230 slopes towards the microfluidic channels from the inlets 210, ports 212, and outlets 214 is between about 10 degrees and about 30 degrees, between about 15 degrees and about 25 degrees, or between about 15 degrees and about 20 degrees. The gradual slope angle of the transition region 230 reduces the likelihood of the cells clumping within the culture device 200. In some implementations, the transition region 230 includes a plurality of channels and the bends within the transition region have angles within the above-defined range. In other implementations, as illustrated in FIG. 4, a top (or floor) of the channels within the transition region is substantially horizontal, and a floor (or top) of the channel slopes and tapers toward the microfluidic channels. In these implementations, the slope or taper of the channels within the transition region 230 is within the above-defined range.

Figure 5:
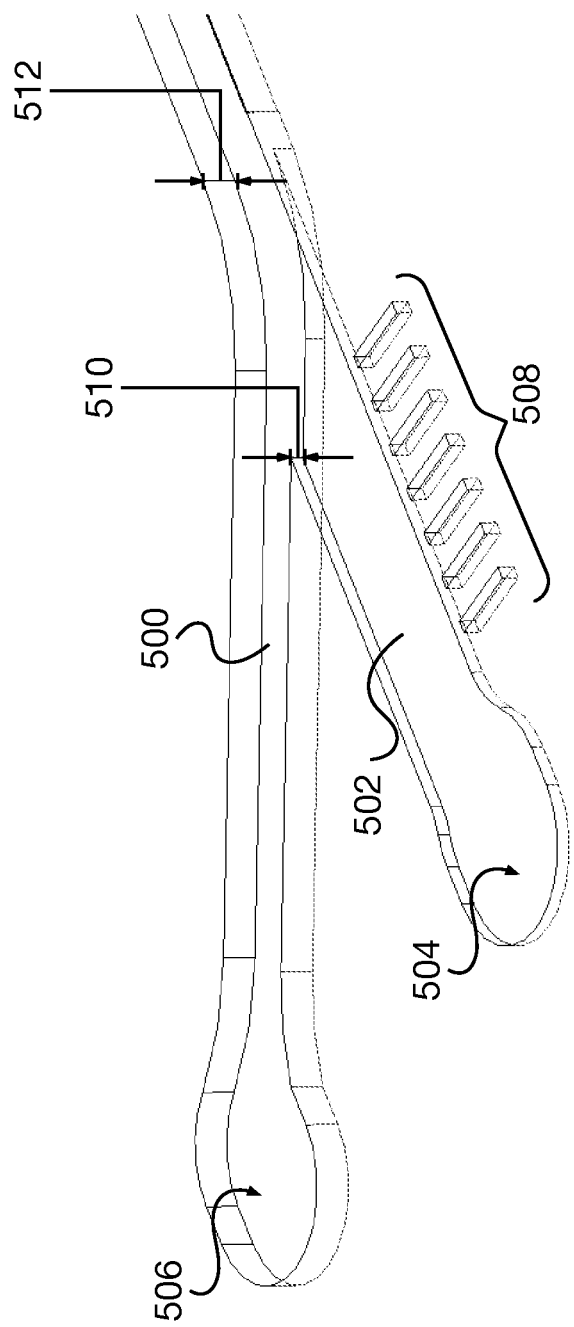
FIG. 5 illustrates an enlarged view of an example graduated microfluidic channel for use in the example culture device illustrated in FIG. 2.

FIG. 5 illustrates an enlarged view of an example graduated microfluidic channel 502. As an overview, the graduated microfluidic channel 502, as described further below, enables the quantification of fluid and chemical flow through the culture device. Fluid flow across the membrane of the culture device creates a transmembrane pressure differential. The pressure differential is caused by both diffusion and convection across the membrane. The pressure differential results in a volume of fluid in each of the microfluidic channels changing. With the valves closed to prevent flow into and out of the microfluidic channels of the culture device, the volume change in each of the microfluidic channels caused by the pressure differential causes a volume change in the graduated microfluidic channel 502. The amount of volume change directly correlates to the distance the fluid travels into the graduated microfluidic channel 502. As illustrated, the microfluidic channel includes one graduated microfluidic channel 502. In some implementations, the microfluidic channels described herein include between 2 and 10 graduated microfluidic channels, between 2 and 8 graduated microfluidic channels, between 2 and 6 graduated microfluidic channels, or between 2 and 4 graduated microfluidic channels. In some implementations, graduated microfluidic channels 502 are also used to inject fluid into and sample from the fluidically coupled microfluidic channel.

Referring to FIG. 5, the graduated microfluidic channel 502 is fluidically coupled to a microfluidic channel 500. In some implementations, the microfluidic channel 500 is similar to the above-described first microfluidic channel 202, second microfluidic channel 204, or any other microfluidic channel described herein. The graduated microfluidic channel 502 includes a port 504 that couples to, for example, the graduated microfluidic channel port 212(a) described above in relation to FIG. 2. The inlet 506 couples to, for example, the inlet 210(a) described above in relation to FIG. 2. A plurality of markings 508 is positioned next to the graduated microfluidic channel 502.

The markings 508 enable precise measurement of how far into the graduated microfluidic channel 502 fluid flows as a result of a pressure differential. For example, a user, using the imager 107 described in relation to FIG. 1, can count the number of markings the fluid flows past. The markings 508 are machined or formed into the polymer layer that defines the microfluidic channel 500 and the graduated microfluidic channel 502. In some implementations, the markings 508 are marked onto the polymer layer by, for example, screen-printing, inkjet or 3D printing or direct printing. In some implementations, the markings 508 are marked with the application of a metal layer to each of the marking areas during the deposition of the metal layer for the herein described electrodes. In some implementations, the distance between each of the markings 508 is between about 50 µm and about 400 µm, between about 100 µm and about 300 µm, or between about 100 µm and about 250 µm.

The graduated microfluidic channel 502 includes a height 510 that is less than a height 512 of the microfluidic channel 500. In some implementations, the height 510 of the graduated microfluidic channel 502 is between about ⅛ and about ⅔, between about ¼ and about ⅝, or between about ¼ and about ½ of the height 512 of the microfluidic channel 500. In some implementations, the height 510 is about ½ of the height 512. The height 512 of the microfluidic channel 500 is between about 50 µm and about 500 µm, between about 50 µm and about 400 µm, between about 50 µm and about 300 µm, between about 50 µm and about 200 µm, or between about 100 µm and about 200 µm tall (or deep). The width of the graduated microfluidic channel 502 and the microfluidic channel 500 is between about 200 µm and about 800 µm, between about 300 µm and about 700 µm, or between about 400 µm and about 600 µm wide. The height 510 of the graduated microfluidic channel is between about 25 µm and about 250 µm, between about 25 µm and about 200 µm, between about 25 µm and about 150 µm, between about 25 µm and about 100 µm, or between about 50 µm and about 100 µm tall (or deep).

Figure 6:
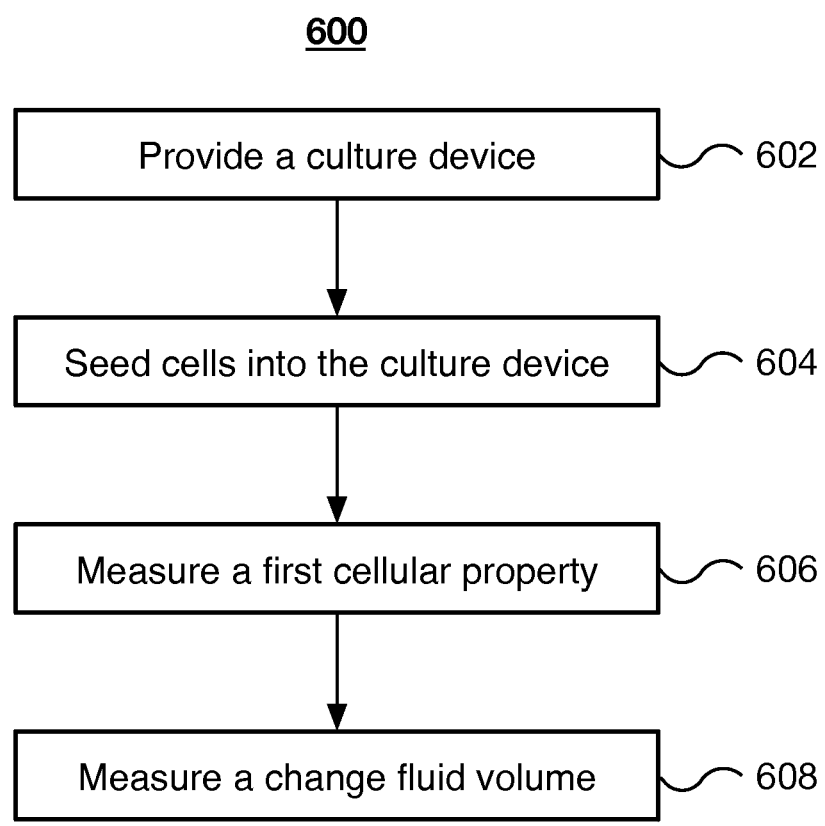
FIG. 6 illustrates a flow chart of an example method for culturing tissue using the example system illustrated in FIG. 1.

FIG. 6 illustrates a flow chart of an example method 600 of culturing tissue. The method 600 includes providing a culture device (step 602). Cells are then seeded into the culture device (step 604). A first cellular property of the cells is measured (step 606). The method 600 also includes measuring a change in a fluid volume (step 608).

As set forth above the method 600 includes providing a cell culture device (step 602). The cell culture device can be any of the cell culture devices described herein. For example, the cell culture device can include a first layer that defines a first microfluidic channel and a first graduated microfluidic channel. The cell culture device also includes a second microfluidic channel and a second graduated microfluidic channel defined in a second layer. A membrane is sandwiched between the first and second layers and separates the first and second microfluidic channels at overlapping portions. The culture device also includes a plurality of electrodes in the first and/or second microfluidic channels.

The method 600 also includes seeding cells into the culture device (step 604). In some implementations, the cells are seeded into the culture device such that the cells form a cellular mat across at least one surface of the membrane of the culture device. The microfluidic channels are configured to enable the cell to be seeded into the culture device without dismantling the culture device. For example, the microfluidic channels of the culture device can be configured to have no abrupt transitions or angles (e.g., by having angles between about 10 degrees and about 30 degrees). The gradual transition enables cells to be flowed to into the middle of the microfluidic channels from the inlets of the microfluidic channels. In some implementations, the cells are kidney cells or endothelial cells from the central nervous system that form the blood brain barrier. In some implementations, experimentation on the cells seeded into the culture device begins once the cells form a cellular mat over at least one surface of the membrane of the culture device.

Next, at least one cellular property is measured (step 606). In some implementations, the cellular property is measured with one or more electrodes of the culture device. For example, the microfluidic channels of the culture device can include electrodes that are configured to measure transepithelial electrical resistance across the membrane and/or the cells cultured on the membrane. In some implementations, a second cellular property is measured after the cells are exposed to a stimulus. For example, a second transepithelial electrical resistance can be measured a predetermined time after the cells are exposed to the stimulus. In some implementations, the stimulus is a pharmaceutical agent, a biological agent, a toxin, a predetermined pressure, a predetermined shear rate, a predetermined flow rate, or any combination thereof. In some implementations, measuring a cellular property can include injecting a tracer molecule into a first graduated microfluidic channel and then measuring the amount of the tracer molecule that is transported to a second graduated microfluidic channel.

The method 600 also includes measuring a change in a fluid volume in at least one of the graduated microfluidic channels of the culture device. In some implementations, prior to measuring a fluid volume in the graduated microfluidic channels fluid flow into and out of the microfluidic channels of the culture device is stopped by closing a fluidic gate or valve in the flow pathway of the microfluidic channels. In these implementations, the change in fluid volume in at least one of the graduated microfluidic channels can be caused by a transmembrane pressure difference that is the result of the transport of fluid across the membrane by the cells cultured on the membrane. In some implementations, the velocity of the fluid flowing into the graduated microfluidic channels is also measured. The velocity of the fluid flow and the amount of fluid flow into the graduated microfluidic channels can be measured by measuring the movement of a detectable interface, such as an air-fluid interface, fluid-fluid interface, or tracer molecule within the graduated microfluidic channel. For example, initially the graduated microfluidic channel can be filled with a gas. In some implementations, the fluid-fluid interface is generated by a difference in concentrations, compositions, viscosities, or other properties of the fluids within the graduated microfluidic channel. As transmembrane pressure difference increases fluid can be driven from a microfluidic channel and into the graduated microfluidic channel coupled with the microfluidic channel. The movement of the fluid into the graduated microfluidic channel is measured as the fluid displaces the gas in the graduated microfluidic channel. In some implementations, a plurality of graduated markings are formed along the graduated microfluidic channel and enable a user to monitor the rate of change or volume of fluid change in the graduated microfluidic channel with a microscope or other imager.

The disclosed system and methods may be embodied in other specific forms without departing from the spirit or essential characteristics thereof. The forgoing implementations are therefore to be considered in all respects illustrative, rather than limiting of the invention.

The invention claimed is:
1. A culture device comprising:
 a first layer having a membrane-adjacent surface and a first microfluidic channel having a recessed surface and two sidewalls defined into the first layer, wherein the two sidewalls connect the recessed surface to the membrane adjacent surface;
 a first graduated microfluidic channel defined into the first layer such that a height of the first graduated microfluidic channel is between about ⅛ and about ⅔ of a height of the first microfluidic channel and the first graduated microfluidic channel is in fluid communication with the first microfluidic channel;
 a second layer having a membrane-adjacent surface and a second microfluidic channel having a recessed surface and two sidewalls defined into the second layer, wherein the two sidewalls connect the recessed surface to the membrane adjacent surface;
 a membrane separating the first microfluidic channel of the first layer from the second microfluidic channel of the second layer and in contact with the membrane-adjacent surfaces of the first and second layers;

a plurality of first electrodes disposed in the first microfluidic channel, wherein the first electrodes cover at least a portion of the recessed surface of the first microfluidic channel; and a plurality of second electrodes disposed in the second microfluidic channel, wherein the second electrodes cover at least a portion of the recessed surface of the second microfluidic channel.

2. The device of claim 1, further comprising a second graduated microfluidic channel in fluidic communication with the second microfluidic channel.

3. The device of claim 1, wherein the first and second electrodes are between about 0.5 μm and about 15 μm thick.

4. The device of claim 2, wherein a height of the second graduated microfluidic channel is between about 1/8 and about 2/3 of a height of the second microfluidic channel.

5. The device of claim 1, further comprising a transition channel between an inlet of the first microfluidic channel and the first microfluidic channel, wherein an angle between a wall of the transition channel and the membrane is between about 10 degrees and about 30 degrees.

6. The device of claim 1, further comprising an imager.

7. The device of claim 1, further comprising at least one valve to control a fluid flow into the first microfluidic channel and the second microfluidic channel.

8. The device of claim 1, wherein the first and second electrodes are configured to measure a trans-epithelial electrical resistance across the membrane.

9. The device of claim 1, wherein the first layer and the second layer comprise a cyclic olefin copolymer.

10. The device of claim 1, wherein the first electrodes run up one of the sidewalls of the first microfluidic channel and extend across a portion of the membrane-adjacent surface of the first layer, and the second electrodes run up one of the sidewalls of the second microfluidic channel and extend across a portion of the membrane-adjacent surface of the second layer.

11. The device of claim 1, wherein the first and second electrodes are less than 15 μm thick.

* * * * *